United States Patent [19]

Haar et al.

[11] Patent Number: 6,074,360
[45] Date of Patent: Jun. 13, 2000

[54] ELECTROMAGNETIC TRANSDERMAL INJECTION DEVICE AND METHODS RELATED THERETO

[75] Inventors: Hans-Peter Haar, Wiesloch, Germany; George B. Kirby Meacham, Shaker Heights, Ohio; Manfred Beuttenmueller, Ladenburg, Germany; Gerhard Winter, Dossenheim, Germany; Markus Mattern, Heppenheim, Germany

[73] Assignee: Boehringer Mannheim GmbH, Mannheim, Germany

[21] Appl. No.: 08/897,433

[22] Filed: Jul. 21, 1997

[51] Int. Cl.[7] .......................... A61M 31/00; A61M 5/30; F41B 6/00
[52] U.S. Cl. ............................. 604/57; 604/59; 604/68; 124/3
[58] Field of Search .................. 604/68, 57–59, 604/890.1, 19, 20, 69, 131; 128/200.14–200.19; 124/3, 54; 89/8

[56] References Cited

U.S. PATENT DOCUMENTS

| | | | |
|---|---|---|---|
| 3,736,933 | 6/1973 | Szabo | 128/216 |
| 3,788,315 | 1/1974 | Laurens | 128/173 |
| 4,301,970 | 11/1981 | Craighero | 128/200.14 |
| 4,432,333 | 2/1984 | Kurherr | 124/3 |
| 4,635,587 | 1/1987 | Hughes | 128/200.14 |
| 4,656,918 | 4/1987 | Rose et al. | 89/8 |
| 4,760,769 | 8/1988 | Jasper, Jr. | 89/8 |
| 4,817,494 | 4/1989 | Cowan | 89/8 |
| 4,858,511 | 8/1989 | Jasper, Jr. | 89/8 |

(List continued on next page.)

FOREIGN PATENT DOCUMENTS

| | | |
|---|---|---|
| 2360031 | 7/1976 | France . |
| 2206794 | 1/1989 | United Kingdom . |
| 2 211 589 | 7/1989 | United Kingdom . |
| 0 371 838 A1 | 11/1989 | WIPO . |
| 0 406 778 A1 | 7/1990 | WIPO . |
| WO 92/04439 | 3/1992 | WIPO . |
| 0 693 119 B1 | 4/1994 | WIPO . |
| WO 94/24263 | 10/1994 | WIPO . |
| WO 96/18425 | 6/1996 | WIPO . |
| WO 97/12194 | 4/1997 | WIPO . |

OTHER PUBLICATIONS

Williams et al. *Proc. Natl. Acad. Sci. USA* vol. 88, (1991) Genetics, pp. 2726–2730.
Oard et al. *Plant Physiol.* (1990) 92, pp. 334–339.

*Primary Examiner*—Sharon Kennedy
*Attorney, Agent, or Firm*—Dike, Bronstein, Roberts & Cushman, LLP; David G. Conlin; William J. Daley, Jr.

[57] ABSTRACT

Featured is a method for injection of a payload into the tissues of an organism or a body, including the steps of generating forces by electromagnetic repulsion and accelerating the payload to be injected, using the generated electromagnetic forces. The payload is thereby accelerated to a velocity sufficient for the payload to pass through the skin of the organism and be disposed in the subcutaneous tissues. The method further includes providing an electromagnetic force generating device that generates forces electromagnetically in a predetermined direction responsive to an electric current flowing through the device, wherein the step of generating includes passing an electric current through the electromagnetic force generating device to generate the electromagnetic repulsive forces used for accelerating the payload. Also featured is a electromagnetic force generating mechanism that includes a conductive member, which is configured so as to generate electromagnetic repulsive forces in a given direction to accelerate the payload responsive to a pulsed current passing through the conductive member. Additionally featured is an electromagnetic transdermal injection device including such an electromagnetic force generating mechanism, an electrical power supply and a switch that selectively interconnects the power supply and force generating mechanism to accelerate a payload such as a medicine.

20 Claims, 9 Drawing Sheets

U.S. PATENT DOCUMENTS

| | | | |
|---|---|---|---|
| 4,922,800 | 5/1990 | Hoffman | 89/8 |
| 4,926,741 | 5/1990 | Zabar | 89/8 |
| 4,960,760 | 10/1990 | Wang et al. | 305/1 |
| 4,966,884 | 10/1990 | Hilal | 505/1 |
| 4,971,949 | 11/1990 | Laskaris et al. | 505/1 |
| 5,042,359 | 8/1991 | Witt et al. | 89/8 |
| 5,105,713 | 4/1992 | Wirgau | 89/8 |
| 5,122,506 | 6/1992 | Wang | 505/1 |
| 5,125,321 | 6/1992 | Cowan, Jr. et al. | 89/8 |
| 5,141,131 | 8/1992 | Miller, Jr. et al. | 222/54 |
| 5,168,118 | 12/1992 | Schroeder | 89/8 |
| 5,173,568 | 12/1992 | Parmer | 89/8 |
| 5,204,253 | 4/1993 | Sanford et al. | 435/172.3 |
| 5,269,327 | 12/1993 | Counts et al. | 128/200.14 |
| 5,294,850 | 3/1994 | Web et al. | 310/13 |
| 5,435,282 | 7/1995 | Haber et al. | 128/200.16 |
| 5,630,793 | 5/1997 | Rowe | 604/20 |
| 5,694,920 | 12/1997 | Abrams et al. | 604/58 |

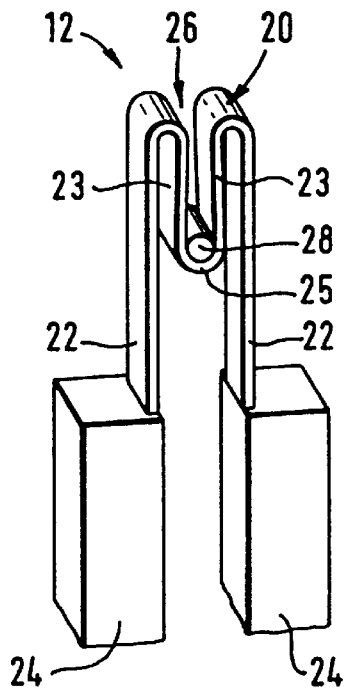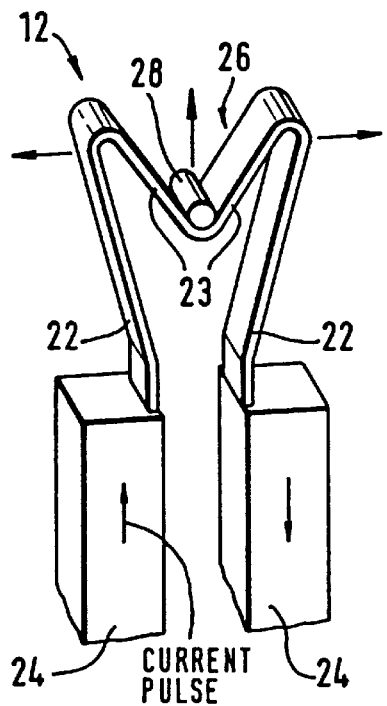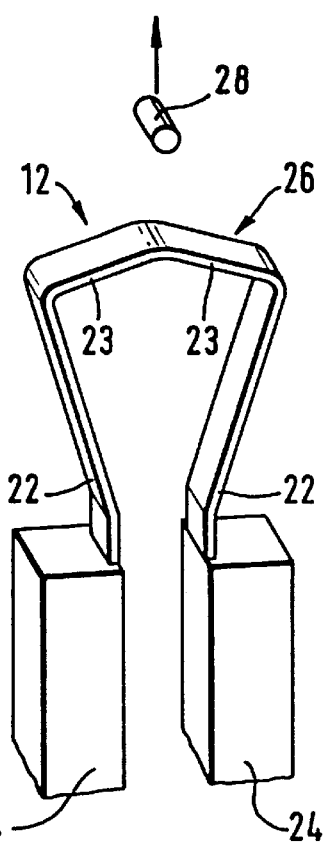
Fig. 1A  Fig. 1B  Fig. 1C
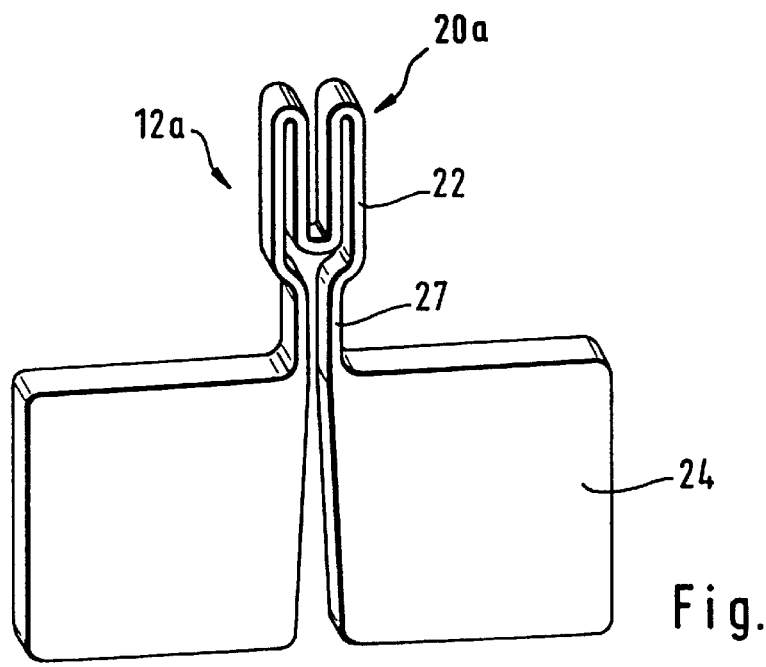
Fig. 2

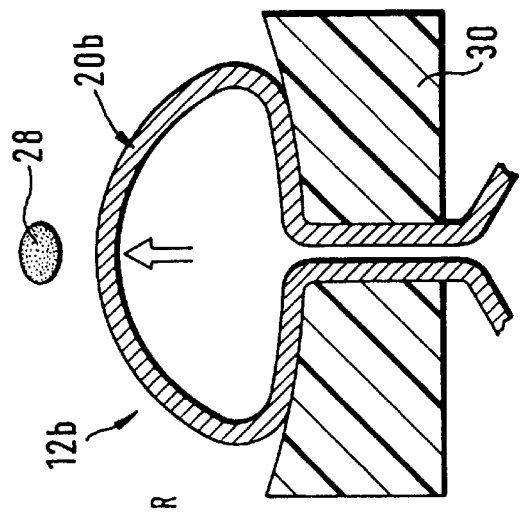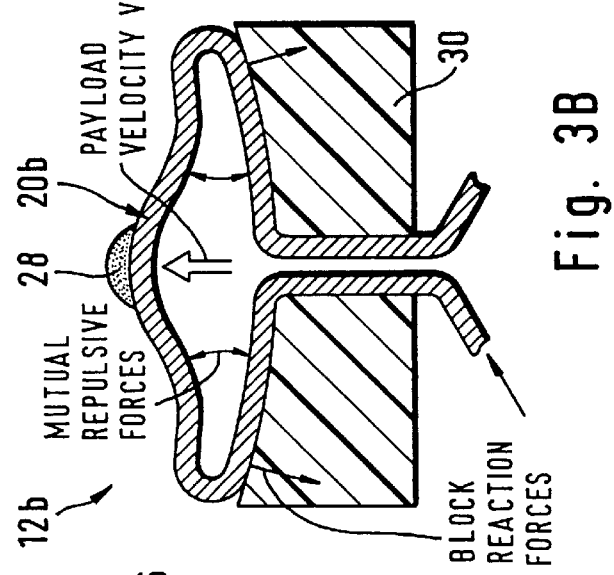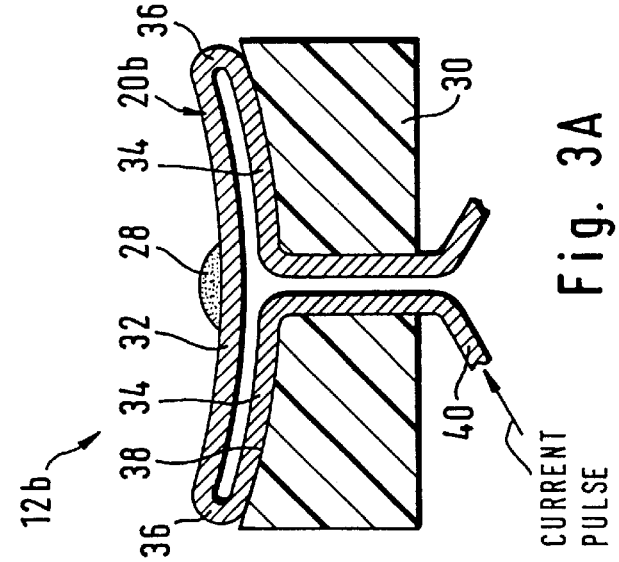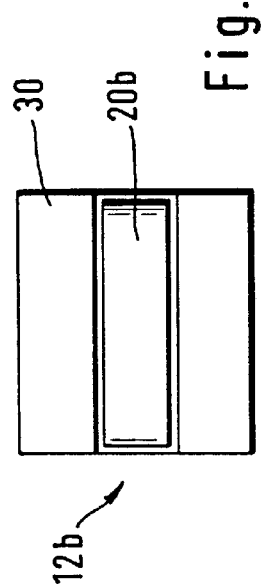

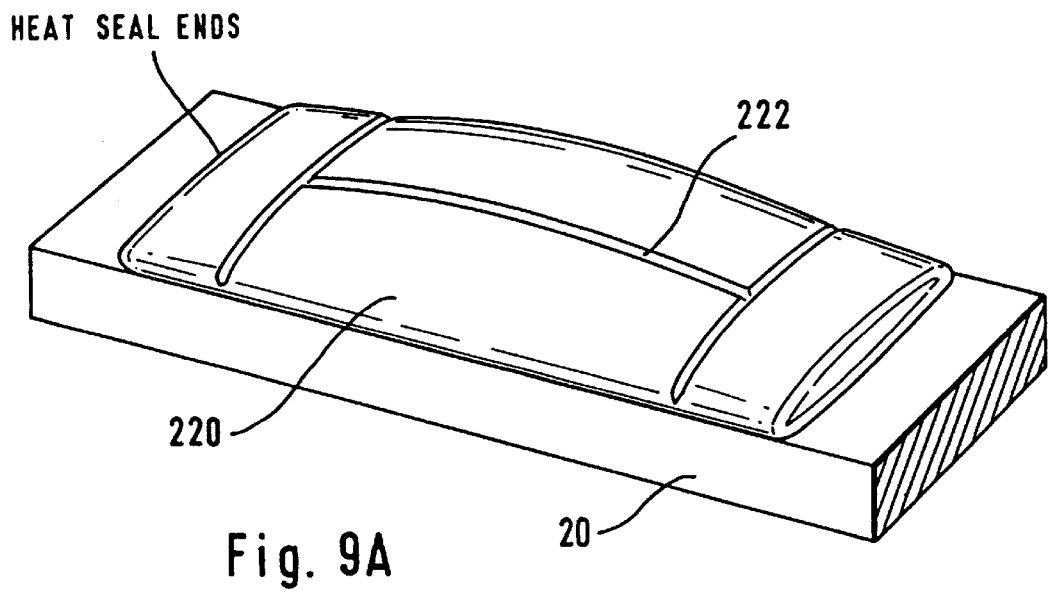
Fig. 9A
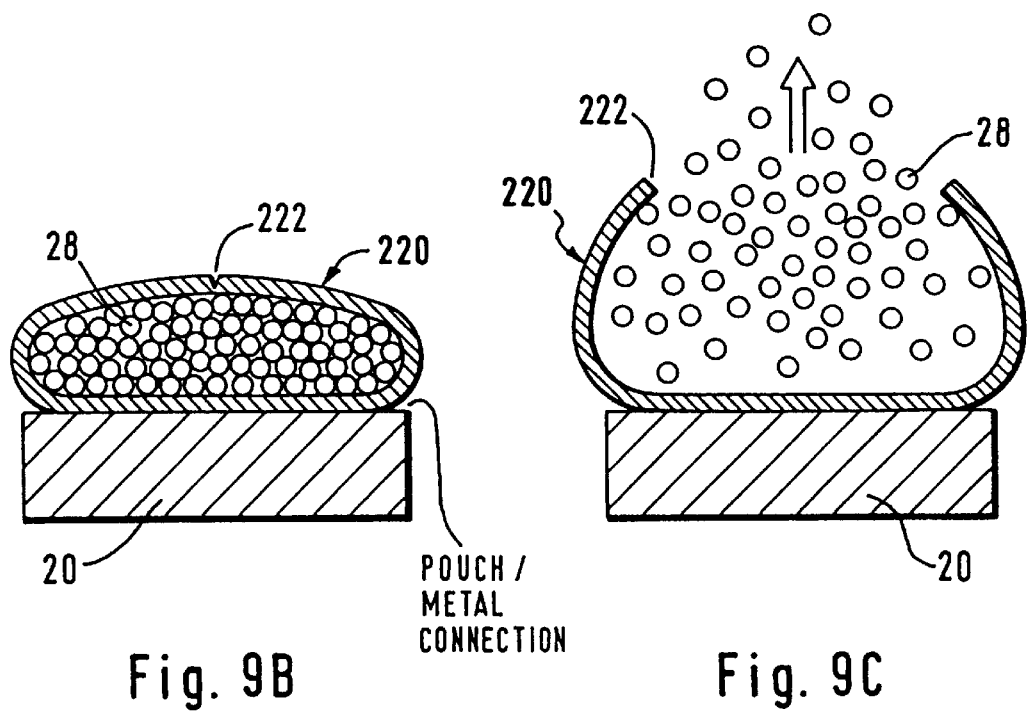
Fig. 9B
Fig. 9C

ELECTROMAGNETIC TRANSDERMAL INJECTION DEVICE AND METHODS RELATED THERETO

FIELD OF THE INVENTION

The present invention relates to a device and methods for injecting substances such as medicines into body tissues and more particularly to methods and devices that inject dry substances into such tissues by means of electromagnetic energy.

BACKGROUND

A number of methods have been employed to dispense medicines or medications. When it is not possible to develop a patient-friendly form of administration, such as an orally administered tablet, it is necessary to introduce the medicine or medication directly into the body tissue or into the vascular blood system. Hypodermic needles are commonly used to inject liquid solutions or suspensions of a pharmaceutical agent into a patient's subcutaneous tissues.

Despite wide usage, hypodermic syringes present notable shortcomings. The sharp hollow needles can cause injury to the patient as well as to the medical personnel administering the injection. The spent needles also are a potential source of infection or means for communication of disease, and consequently the used needles must be handled as hazardous medical waste. The injections are generally painful because of the needle's penetration of the patient's skin and the volume (e.g., 0.01 to 0.5 ml) of the injected fluid. Additionally, administration by injection can require good eyesight and dexterity. This can be a problem for many patients who self-administer their injections. Thus, the overall process of administering an injection using the hypodermic syringe technique can be relatively costly, time-consuming and complex.

Liquid jet injection systems have been developed as a needle-free alternative to the hypodermic syringe. By that approach, a jet of liquid is ejected from an orifice at a high velocity that is capable of penetrating through tissue so as to deposit the medication subcutaneously. In comparison to hypodermic syringes, a liquid jet injections system may be less painful and may have a lower skill requirement for the user. The persons being injected also exhibit less psychological aversion to a liquid jet injection system than those being injected by means of a hypodermic syringe.

However, drug delivery by a liquid jet can cause skin damage and bleeding. Additionally, a relatively large amount of energy is required to displace the liquid volume and form the high velocity jet, e.g. pressures on the order of several hundred atmospheres. Although theoretical energy requirements are about 6 joules of mechanical energy in a period of about 200 milliseconds, mechanical and other system losses result in an actual energy requirement that is significantly higher, e.g. about 10 to 20 joules. The means for generating this large energy pulse includes large springs, compressed gas and pyrotechnic actuators. From a size and performance standpoint compressed gas and pyrotechnics are advantageous, however, they face regulatory barriers common to such devices for example the safety limitations or regulations on shipping and handling.

In addition for the hypodermic syringe technique or liquid injection system, the shelf life of liquid solutions or suspensions to be injected is most often less than that for dried powdered forms of medications or medicines. Consequently, some sensitive medications must be stored as dry powder and then mixed with a sterile liquid immediately prior to use. The process of preparing the solutions or suspensions for injection requires specialized skill and training as well as being time consuming and costly. Additionally, in less developed regions special preparations are usually required to provide an adequate source of sterile fluid and/or maintain the liquid solutions or suspensions.

PCT Publication No. WO 94/24263 reports a certain needleless syringe using supersonic gas flow for delivery of dry particles including therapeutic agents. In this needless syringe, at least one membrane is ruptured by a highs pressure gas source to generate a supersonic gas flow. In a particular embodiment, the publication describes using a small 60-atmosphere reservoir of helium as the gas source. As described therein, the rupturing of the membrane and the supersonic gas flow causes the medication particles to be accelerated to a velocity of about 800 to 1000 meters per second. It is also reported that the particles so accelerated penetrate a patient's skin to thereby deliver the medication. That described system has a number of shortcomings. The described syringe requires a high-pressure gas reservoir and release mechanism, or a mechanical equivalent, to generate the pressures required to establish supersonic flow conditions. Also, supersonic flow is noisy, and measures must be taken to reduce sound output. Thus, the PCT Application describes (e.g., at page 14) a silencer to receive the shockwave reflected back from the patient's skin. Despite the silencer, the device is very loud as a result of the fast release of high-pressure gas. Still further, because the system described in the PCT Application uses a pressurized gas source, the system faces regulatory barriers as with liquid jet injection systems that employ compressed gas.

It thus would be desirable to have new methods and devices for administering therapeutic agents to a patient. It would be particularly desirable to have new methods and devices that could administer dry therapeutics through a patient's skin. Such devices and methods preferably would be simple in construction, be less costly per injection than prior art devices and methods, would not require highly skilled users to utilize the device, would prove to be less painful than an injection administered by means of a hypodermic syringe and would prove to be less noisy than prior art devices.

SUMMARY OF THE INVENTION

In a preferred aspect, the invention features a transdermal injection device for injecting a therapeutic agent into a body through use of electromagnetic repulsive forces.

By the methods and devices of the invention, dry powders, particles or substances can be injected through the skin of a body, e.g. human, animal or plant. Dry powders or particles or other materials can be administered whereby the material resides in subcutaneous tissue of the body.

In general, the dry substances being injected include, but are not limited to, solids, gels, liquids absorbed into porous solids, encapsulated liquids, powders or any form of material that can be injected at and/or accelerated to a high velocity. The particles and the like can be irregular in shape as well as being in predetermined forms or shapes, for example, spheres or arrows. The particles and the like can be uniform in size or vary over a prespecified range of sizes, for example, on the order of microns. Also, the number thereof can range from one to a million or more.

In general, a device of the invention uses electromagnetic repulsive forces between conductors carrying high anti-parallel pulsed currents to actuate a slingshot-like mechanism. This slingshot-like mechanism accelerates the material to be administered to a velocity sufficient for injection into a body. The material to be administered can be any of a variety of materials, particularly therapeutic agents such as insulin, antibiotics, analgesics, etc.

Other aspects of the invention are discussed below.

BRIEF DESCRIPTION OF THE DRAWING

For a fuller understanding of the nature and desired objects of the present invention, reference is made to the following detailed description taken in conjunction with the accompanying drawing figures wherein like reference characters denote corresponding parts throughout the several views and wherein:

FIGS. 1A–1C are schematic views of a first embodiment of a slingshot mechanism that show the principle embodied in the present invention;

FIG. 2 is an axonometric view of an alternate embodiment of the slingshot mechanism of FIGS. 1A–1C;

FIGS. 3A–3C are cross sectional views of a second embodiment of a slingshot mechanism that show the principle embodied in the present invention;

FIG. 3D is a top view of an exemplary embodiment for the slingshot mechanism of FIGS. 3A–3C;

FIGS. 9A–9C illustrate a third exemplary payload packaging arrangement;

DETAILED DESCRIPTION OF THE INVENTION

Figure 4:
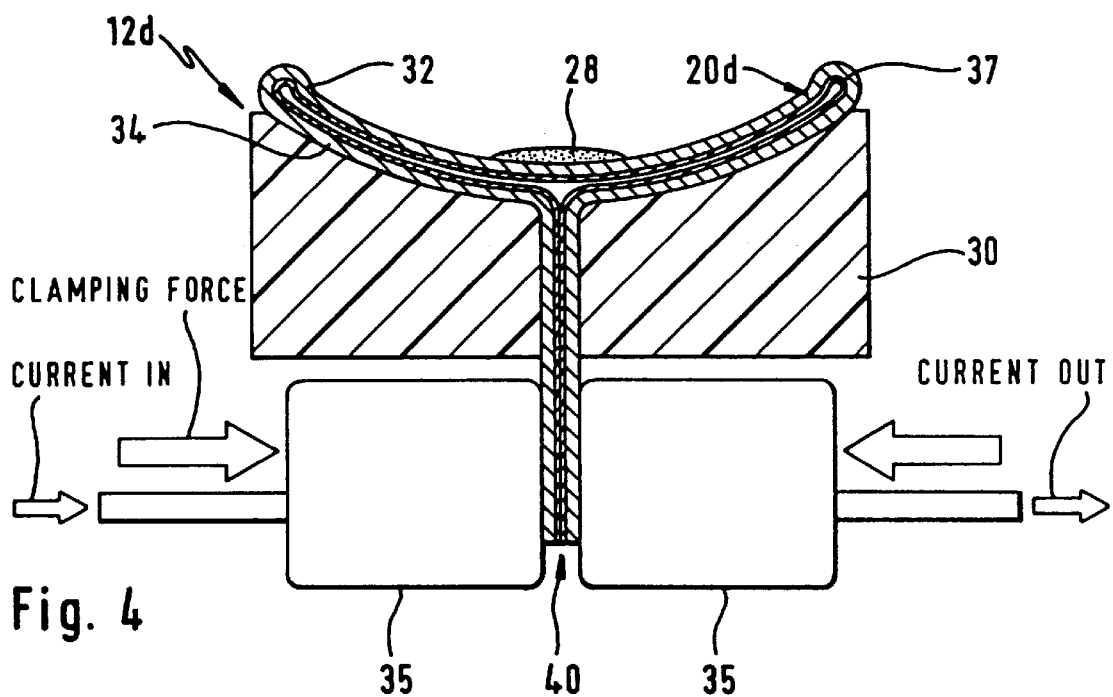
FIG. 4 is a cross sectional view of an alternate embodiment of the slingshot mechanism of FIGS. 3A–3D.

The present invention includes an injection device for injecting a payload, particularly a dry powder, particles or the like, into and through the skin of a body, be it human, animal or plant. Electromagnetic repulsive forces between conductors carrying anti-parallel pulsed currents accelerate the payload to a sufficiently high velocity for injection into the body. For the instant invention anti-parallel, is intended to describe the initial conditions of the current as it flows through the conductors. Specifically, that the current flow in one conductor is parallel to the flow in a second conductor but flowing in a different direction vectorally.

In a particular embodiment, the mechanism for generating the repulsive forces includes first and second conductive members that are initially disposed so that at least in a specified region the first and second conductive member are essentially parallel to each other. The payload is releasable attached or secured to the second conductive member in any of a number of ways so it is retained thereon while the repulsive forces are accelerating it. Where the repulsive forces are generated by passing a current through the first and second conductive members so the second conductive member is repulsively moved away from the first conductive member in at least the specified region whereat the first and second members are initially disposed parallel to each other. The payload also is attached or secured to the second member so it is released therefrom at an appropriate point during its acceleration.

In the following, various specific configurations for a slingshot mechanism are described and illustrated, however, the injection device and methods related thereto of the instant invention are not limited to these specific configurations. It is within the scope of the instant invention to provide a conductive metal member 20 having any geometric configuration that will, when subject to a high voltage, pulsed current, generate a force in a predetermined direction, which force accelerates a payload to the desired velocity for purposes of injection.

Typically the geometric configurations of a given slingshot mechanism 12 includes at least three attributes. First, the configuration of the slingshot mechanism suitably allows at least two opposing conductive members to be disposed as close as possible to each other with almost zero inductance. Preferably, the configuration arranges the metal members so at least a portion of one metal member is essentially parallel to the other metal members over a pre-specified distance.

Secondly, when a pulsed current is passed through the metal members, the configuration of the slingshot mechanism suitably allows at least one of the metal members to move repulsively way from the other metal member. Preferably, the configuration establishes anti-parallel current flow in opposing metal members in the pre-specified region so the at least one member is moved and accelerated by the electromagnetic fields created by the anti-parallel currents.

Thirdly, the repulsive motion of the at least one metal member results in at least a portion of the metal member being accelerated in a predetermined direction. Preferably, the configuration also allows a payload to be mechanically and releasable secured or attached thereto so it also is so accelerated. Additionally, such motion preferably occurs with minimum energy losses to the material.

Referring now to the various figures of the drawing wherein like reference characters refer to like parts, there is shown in FIGS. 1A–1C, schematic views of one embodiment of a slingshot injection mechanism 12 that illustrates the principle embodied in an electromagnetic injection device 10 according to the present invention. Specific reference also should be made to FIGS. 10–12 for those components referred to herein that are not specifically shown on FIGS. 1A–1C. Additionally, reference should be made to FIGS. 7–9 for further details regarding the payload 28, its composition and its attachment to the slingshot injection mechanism 12. For clarity, reference is made to motion in an upwardly or upward direction, however, this is not a limitation as the direction of motion is related to the orientation of the electromagnetic injection device 10 to the targeted area of the body.

FIGS. 1A–1C illustrate the overall operational sequence of the first embodiment of a slingshot mechanism 12 from the pre-injection state or initial position, as illustrated in FIG. 1A, through acceleration of the payload 28, as illustrated in FIG. 1B, and separation of the payload 28 from the slingshot mechanism 12 for injection, as illustrated in FIG. 1C. Referring now only to FIG. 1A, there is shown one embodiment of a slingshot mechanism 12 including a conductive metal member 20, that is bent or shaped into a narrow "M" shape. The two outer arms 22 thereof are bonded or electrically interconnected to input power leads 24. The inner portion of the "M" shape includes two inner arms 23 that are interconnected by an arcuate or bent cup member 25 to form a sling 26. The payload 28 is disposed in the bent cup 25 of the sling 26. The outer and inner arms 22,23 also are mechanically and electrically interconnected by means of curved members that essentially form a hinge point for adjacent inner and outer arms.

When the payload 28 is to be injected, a current pulse is introduced into the slingshot mechanism 12 via the input power leads 24. As the current passes through the metal member 20, the current in each outer arm 22 of the slingshot mechanism 12 is anti-parallel to that in an adjacent inner arm 23. This causes mutual repulsion between adjacent inner and outer arms 22,23 so they move apart from each other as illustrated in FIG. 1B. As the outer and inner arms 22,23 move apart from each other, the bent cup member 25, and correspondingly the payload 28 is accelerated in an upwardly direction, as also illustrated in FIG. 1B. In this way, the motion of the sling 26 transfers kinetic energy developed by the repulsive motion of the inner and outer arms 22,23 to the payload 28.

Further motion of the slingshot mechanism 12 can be best understood by modeling it as a hinged rigid body. Because of mutual repulsion, the outer and inner arms 22,23 continue to move apart until the sling 26 is straightened. At that time, the payload 28 and the relative center of the sling 26 reach their maximum velocity. As the sling 26 passes through the straight position, it starts to slow down. The reduced velocity of the sling 26 causes the payload 28 to separate therefrom as shown in FIG. 1C. The payload 28 continues traveling towards the targeted area of a body. The maximum velocity attained by the payload 28 is sufficient so the payload can penetrate the skin of a body and comes to a rest in the subcutaneous tissues.

The current pulse introduced into the slingshot mechanism 12 preferably is a high current pulse, e.g. on the order of thousands of amperes, over a very short duration, e.g. on the order of microseconds. In this way, the current pulse can pass through the outer and inner arms 22,23 before the arms have moved apart repulsively due to the electromagnetic fields generated by the current pulse. In a preferred embodiment the peak current of the current pulse is in the range of 6,000 to 20,000 amperes, the pulse duration is 1 microsecond or less, and the voltage is in the range of 1,000 to 4,000 volts.

The duration, current and voltage of the current pulse is selected so the maximum velocity attained by the dry substance being injected is sufficient to penetrate the skin of the body or organism and achieve the desired penetration into the tissues thereof. The amount of penetration, and correspondingly the maximum velocity required to be attained, is dependent upon a number of factors including the density, size, orientation and shape of the dry substance or that comprising the dry substance (e.g., particle size). For example, a payload of 0.5 milligrams consisting of particles in about the 20 micron range typically would penetrate the skin and reside in the subcutaneous tissues of a body, if accelerated to a maximum velocity of 800 meters per second or more. However, maximum velocities higher or lower than 800 meters per second can be utilized to achieve the desired penetration for a given size, shape and density of a particle.

The conductive metal member 20 can be made from any of a number of conductive materials and have any thickness provided that the resultant product can accelerate the payload to attain the desired or required velocity for injection of the payload into a patient. Preferably, the materials and thickness selected are sufficient to maintain structural integrity of the slingshot mechanism 12, in particular the metal member 20, following the introduction of the current pulse in the metal member and creation of the repulsive electromagnetic fields to accelerate the payload 28. Additionally, the thickness or configuration of each outer arm 22 can be adjusted to be more resistant to local bending stresses caused by the repulsive force. For example, each outer arm 22 can be provided with a U-shape or the outer arms made thicker than the inner arms 23. In a specific embodiment, the metal member 20 and input leads are made from aluminum. In this specific embodiment, the metal member preferably is a ribbon having a thickness of about 0.1–0.2 millimeters and a width on the order of 1–2 millimeters.

Preferably, the outer and inner arms 22,23 are initially spaced parallel to each other in a pre-specified region on the order of 2–5 millimeters in length. Additionally, the outer and inner arms 22,23 are spaced as close as possible to each other without electrically shorting out across the arms. In particular embodiments, the air gap between the outer and inner arms 22,23 is about 0.025 to about 0.1 millimeters in at least the pre-specified region. Alternatively, and as shown in FIG. 4, an insulating film such as a polymer film is disposed at least between the outer and inner arms 22,23 so the arms are spaced from each other by the thickness of the film. This insulating film also, can be laminated along one surface of the metal member 20 so the film is disposed between the outer and inner arms 22,23.

There is shown in FIG. 2 an alternate embodiment of a slingshot mechanism 12a to that shown in FIGS. 1A–1C. In this embodiment, the conductive metal member 20a includes an intermediate portion 27, including two electrical leads that are electrically and mechanically interconnected to the outer arms 22 and the input leads 24. In all pertinent respects, however, the alternate embodiment functions in a similar fashion as that described hereinabove the slingshot mechanism 12 of FIGS. 1A–1C.

Now referring to FIGS. 3A–3C, there are shown cross-sectional views of a second embodiment of a slingshot injection mechanism 12b that illustrate the principle embodied in an electromagnetic transdermal injection device 10 according to the present invention. Specific reference should be made to FIGS. 10–12 for components referred to herein that are not specifically shown on FIGS. 3A–3C. Additionally, reference should be made to FIGS. 7–9 for further details regarding the payload 28, its composition and its attachment to the slingshot injection mechanism 12. FIGS. 3A–3C illustrate the overall operational sequence of the second embodiment from the initial position, as illustrated in FIG. 3A, through acceleration of the payload 28, as illustrated in FIG. 3B, and separation of the payload 28 from the slingshot mechanism 12b, as illustrated in FIG. 3C.

Referring now only to FIG. 3A, the second embodiment of the slingshot mechanism 12b includes a conductive metal member 20b and a support block 30. The metal member 20b includes an arcuate top portion 32 and two arcuate bottom portions 34, which are interconnected by two curved portions 36. At least a portion of the top surface 38 of the support block 30 is curved to complement the arcuate shape of the bottom portions 34 and includes a through aperture for the conductor leads 40 extending from the bottom portions. The conductor leads 40 are electrically interconnected to the input power leads 24 as illustrated in FIGS. 1–2. In a specific embodiment, as more clearly shown in FIG. 3D, the conductive metal member 20b lies in a dished slot formed in the support block 30.

When the payload is to be injected, a current pulse is introduced into the slingshot mechanism 12b via the input leads 40. Because of the antiparallel currents in the top and bottom portions 32,34, the top and bottom portions are mutually repulsed from each other, as described hereinabove. The motion of the bottom portions 34, however, is essentially restrained by the support block top surface 38. Thus, the mutual repulsive forces mainly cause the top portion 32 to move away from the bottom portions 34 as illustrated in FIG. 3B and thereby accelerate the payload 28. In this way, the slingshot mechanism top portion 32 transfers kinetic energy to the payload 28.

At a certain point in its upward motion, the relative center of the top portion 32 reaches a maximum velocity and thereafter velocity reduction begins. As the top portion 32 begins to reduce velocity, the payload 28 separates from the top portion as shown in FIG. 3C. As described above, the maximum velocity attained by the payload 28 due to the motion of the top portion 32 is sufficient so the payload can penetrate the skin of a body and come to rest in the subcutaneous tissues thereof. Also, the initial curved configuration of the metal member 20b is beneficial in this regard because it enables the metal member to accelerate with minimum bending energy loss and thus, more of the repulsive energy is directed to accelerating the payload. Bending losses are minimized because the bottom portions 34 are being restrained and supported by the support block 30 and because the metal member 20b essentially unrolls from the initial position to the release position without large deformations at the hinge points.

Reference should be made to the foregoing discussion concerning FIGS. 1A–1C for acceptable materials and construction details for the conductive metal member 20b and the parameters or characteristics of the pulse current being injected into the slingshot mechanism 12b. The support block 30 is constructed from materials that can withstand the structural load imposed by the repulsive forces and restrain the bottom portions 34 from further motion. Preferably the materials of the support block are non-conductive and nonmagnetic. In a specific embodiment, the support block is made from ceramics or plastics such as thermoplastics or thermosetting plastics.

There is shown in FIG. 4 an alternate embodiment of a slingshot mechanism 12d to that shown in FIGS. 3A-3D. In this embodiment, an insulating film 37, such as plastic polymer film, is disposed between and electrically isolates opposing surfaces of the top portion 32 and the bottom portions 34 of the conductive metal member 20d. The insulating film 37 also continues along the entire length of the opposing surfaces so as to electrically isolate the two electrical leads 40 that extend outwardly from an aperture in the support block 30. Preferably, the insulating film 37 is applied or laminated to the metal material from which the metal member 20d is formed. Alternatively, any one of a number of techniques or means known to those skilled in the art can be used to separate and electrically isolate the opposing surfaces of the metal conductive member 20d. Also, although lamination of one surface is illustrated, it is within the scope of the instant invention for more than one surface to be laminated or coated with an insulating film.

The leads 40 are interconnected to the current and voltage source by means of two clamping electrodes 35 that clamp the leads together. These clamping electrodes 35 can be included as part of the slingshot module 110 or the plug connection 112 (FIGS. 11–13) so they removably receive the leads 40 of the slingshot mechanism. In all pertinent respects, however, the alternate embodiment functions in a similar fashion as that described hereinabove for the slingshot mechanism 12b of FIGS. 3A–3D.

Figure 5:
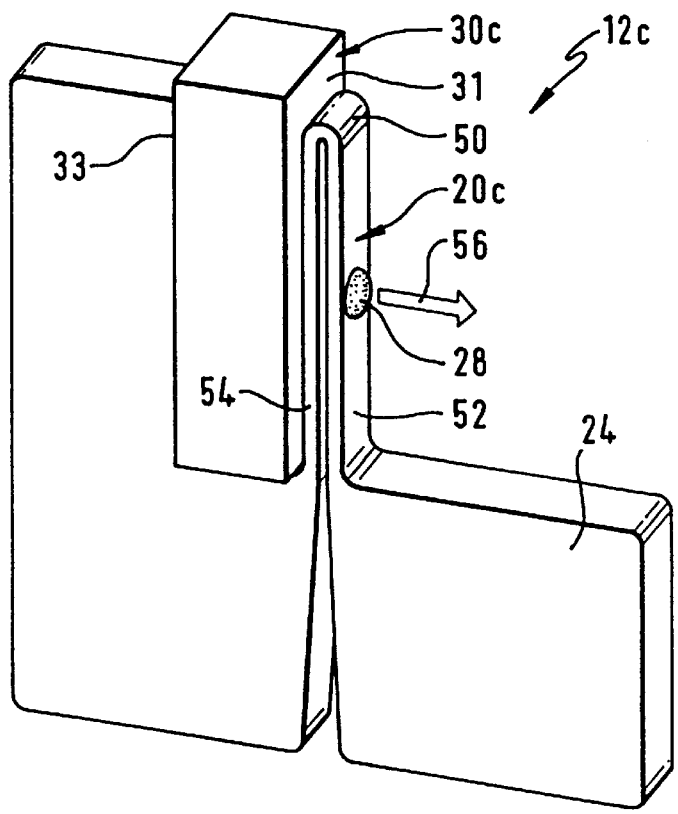
FIG. 5 is an axonometric view of a third embodiment of a slingshot mechanism of the present invention.

There is shown in FIG. 5, a third embodiment of a slingshot mechanism 12c of the instant invention including a conductive metal member 20c, and a support block 30c. Reference should be made to the foregoing discussion regarding FIGS. 1–3 for acceptable materials and construction details for the conductive metal member 20c, the parameters or characteristics of the injected pulse current and the materials for the support block 30c. Also, reference should be made to FIGS. 7–9 for further details regarding the payload 28, its composition and its attachment to the slingshot injection mechanism 12. The metal member 20c includes a loop 50 having first and second arms 52,54 that are mechanically and electrically interconnected to each other by means of a curved portion and which are each mechanically and electrically interconnected to the input power leads 24. The payload 28 is disposed at about the mid-point of the first arm 52.

Figure 13:
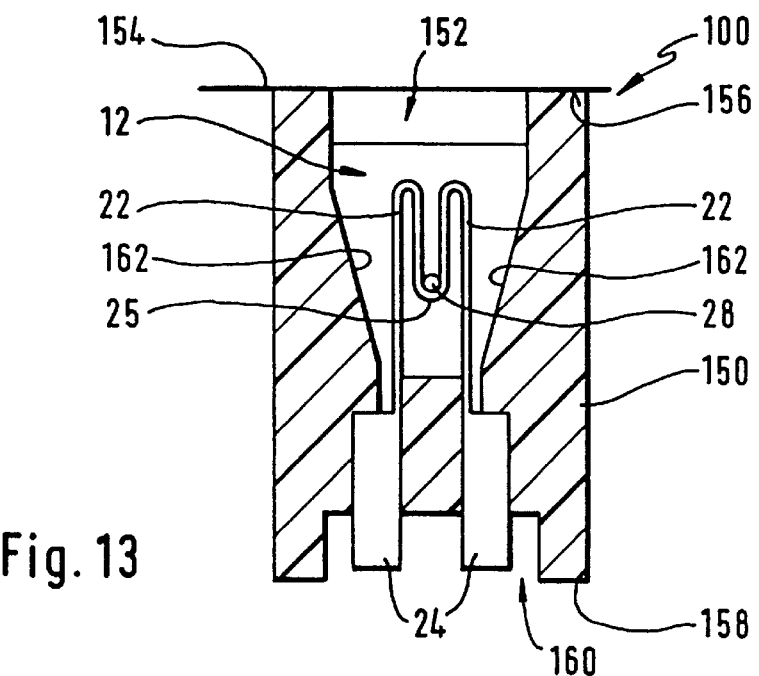
FIG. 13 is a cross sectional view of a slingshot mechanism injection module for use in the injection devices of FIGS. 11–13.

The support block 30c is disposed so one side 31 thereof abuts one side of the second arm 54, preferably this side 31 of the support block is in close contact with this side of the second arm. The opposing side 33 of the support block 30c is in close contact with another non-moving surface of the slingshot module 100 or in a pocket formed in one of the input leads 24, as illustrated in FIG. 5. Alternatively, as illustrated in FIG. 13, the housing 150 for the slingshot module 100 can be configured so the support block is integrally formed as part of the module housing.

To accelerate the payload 28 for injection, a pulsed current is introduced into and passed through the metal member 20c, thereby creating repulsive forces that move the first and second arms 52,54 apart from each other. However, and as described above, the support block 30c essentially restrains the repulsive motion of the second arm 54 so only the first arm 52 moves in any significant fashion in predetermined direction 56. The payload 28 is thus accelerated and moved in this direction in a similar fashion as that described for the top portion 32 of the second embodiment (FIGS. 3A–3C). Also in this way, the payload 28 is accelerated to its maximum velocity and separated from the first arm 52 so it can penetrate the skin of a body and come to rest in the subcutaneous tissues thereof.

Figures 6A, 6B:
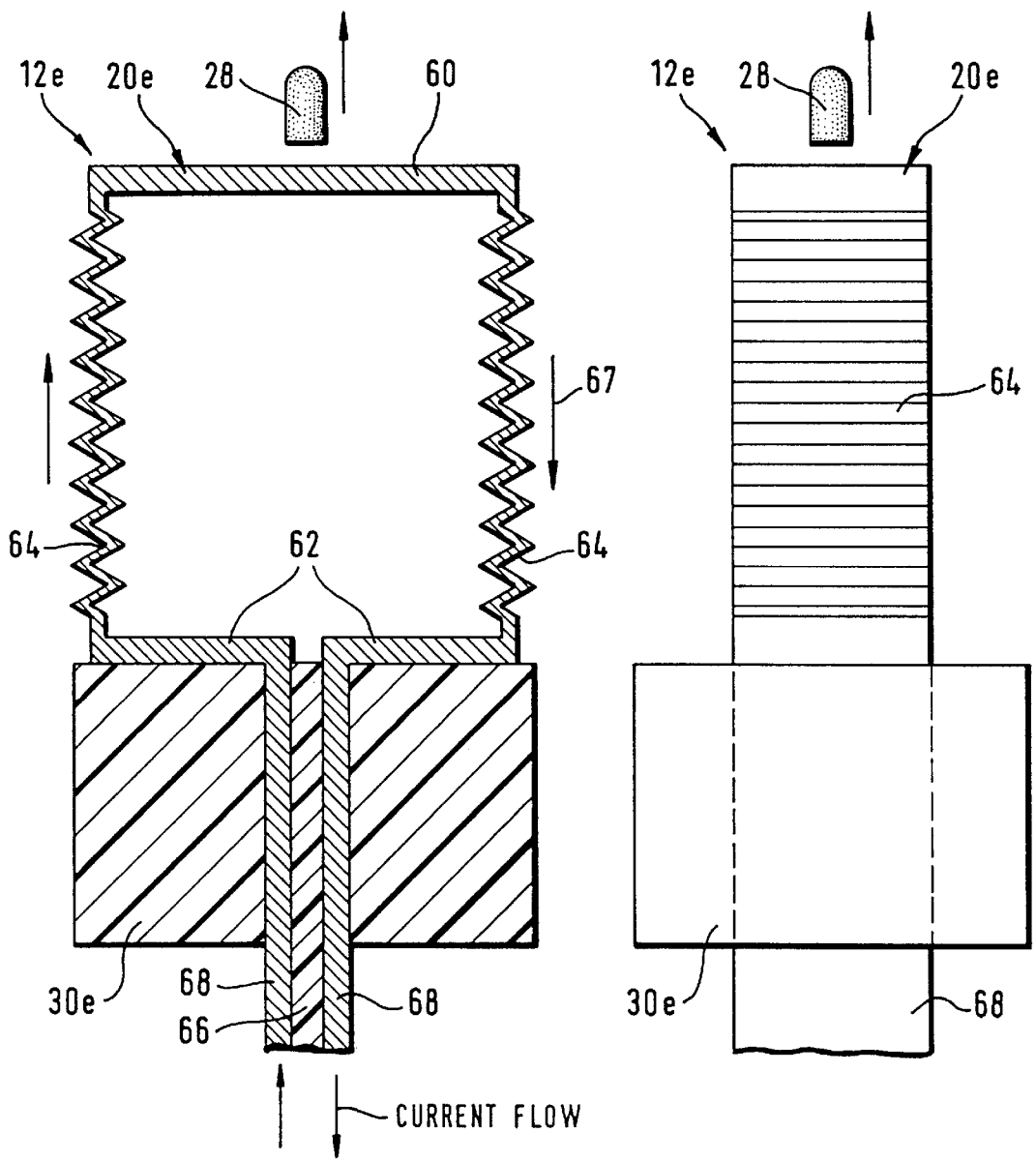
FIGS. 6A–6B are cross sectional and side views respectively of a fourth embodiment of a slingshot mechanism of the present invention.

There is shown in FIGS. 6A–6B a fourth embodiment of a slingshot mechanism 12e of the instant invention including a conductive metal member 20e, and a support block 30e. Reference should be made to the foregoing discussion regarding FIGS. 1–3 for acceptable materials and construction details for the conductive metal member 20e, the parameters or characteristics of the injected pulse current and the materials for the support block 30e. Additionally, reference should be made to FIGS. 7–9 for further details regarding the payload 28, its composition and its attachment to the slingshot injection mechanism 12e.

The metal member 20e includes a top segment 60 that is disposed opposite two bottom segments 62. The top and bottom segments 60,62 are structurally and electrically interconnected to each other by means of two corrugated or fan folded sides 64 so as to for a box like structure having flexible sides. The input leads 68 interconnected to the bottom segments 62 are electrically separated from each other by means of an insulating member 68 that can be an insulating polyester film as hereinabove described. As also described hereinabove, the outside surface and/or the opposing surface of the metal member segments 60,62,64 can be coated with an insulating film as shown in FIG. 4.

Initially, the corrugated sides 64 are compressed downwardly in direction 67 so the top and bottom portions 60,62 are spaced about 0.025 to about 0.1 millimeters apart. To accelerate the payload 28, a current pulse is passed through the metal member 20e via the input leads 68. In a similar fashion to that described above for FIGS. 3A–3C, the bottom segments 62 remain essentially stationary due to the presence of the support block 30e. Thus, the top segment 60 is electromagnetically and repulsively moved away from the bottom segments 62. The corrugated sides 64 also contribute to the repulsive motion of the top segment 60 because of the anti-parallel current flow through opposing corrugations in the corrugated sides. As also described above, at a point during acceleration the payload 28 will separate from the top segment 60 as is shown in FIG. 6A.

There is shown in FIGS. 7–9 three exemplary mechanisms and techniques for packaging the payload 28 so it is releasably attached or secured to a portion of the slingshot mechanism 12 and more specifically to the metal member 20 of such a mechanism. The mechanisms and techniques described herein are not exhaustive of all the possible mechanisms and techniques for holding the payload during it acceleration phase to a member and then controllably releasing it at some point when the payload has attained the maximum velocity desired for injection. As such it is within the scope of the instant invention to include all such other mechanisms, techniques or methods.

The payload 28 comprises dry substances or the like that can be injected through the skin of a body or organism whereby the injected material resides in the subcutaneous tissue of the body or organism. The dry substances being injected include, but are not limited to, solids, gels, liquids absorbed into porous solids, encapsulated liquids, dry powder, particles or any form of material that can be injected at, and/or accelerated to, a high velocity. The particles and the like can be irregular in shape as well as being in predetermined forms or shapes. For example, the particles can be spherical or arrow shaped or a mixture thereof. Further, the particles and the like can be uniform in size or vary over a prespecified range of sizes. Also, the numbers thereof can range from one to a million or more.

In specific embodiments the active material being injected includes therapeutic agents such as antibiotics, insulin, proteins and analgesics. However, it is within the scope of the instant invention for the material being administered to include other injectable substances including for example DNA.

Figure 7A:
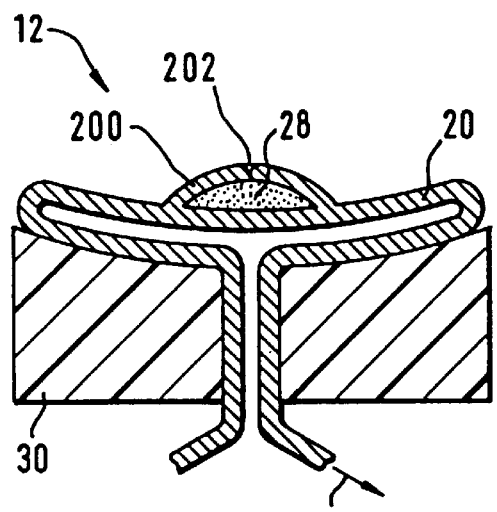
FIGS. 7A–7B illustrate one exemplary payload packaging arrangement.
Figure 7B:
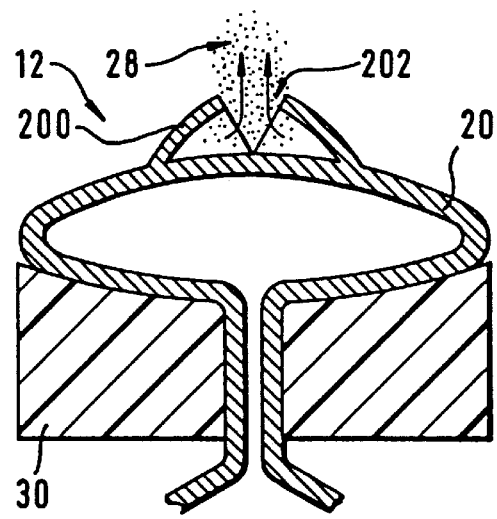

Referring now to FIGS. 7A–7B, there is shown a cross sectional view of part of an exemplary slingshot mechanism 12 to illustrate one mechanism or technique for releasably securing a payload to the slingshot mechanism. In this technique an enclosure is secured to the moving arm or portion of the conductive metal member 20 of the slingshot mechanism 12 using an adhesive or the like. The enclosure 200 includes one or more breaklines 202, slits, areas of localized thinning or the like, which are designed to fail when subject to certain loads and thereby open up the enclosure. As shown in FIG. 7A, when the slingshot mechanism is in its initial, non-accelerated condition, the enclosure is sealed and the payload 28 is retained therein.

When the pulsed current is passed through the conductive metal member 20, the enclosure 220 and correspondingly the payload 28 therein is accelerated in the fashion-described hereinabove. At a point in the acceleration process the inertia of the payload and/or the deformation of the metal member 20 causes each breakline to open thereby releasing the payload 28 for injection as shown in FIG. 7B. Once released, the payload 28 continues onto the targeted area of the body or organism.

Figure 8A:
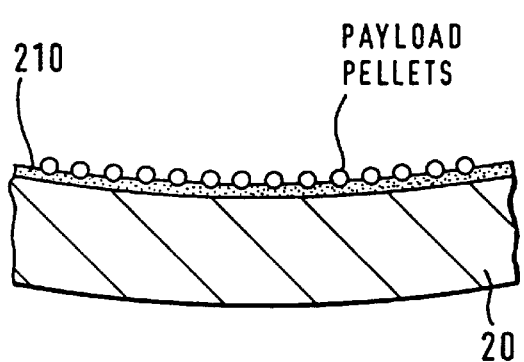
FIGS. 8A–8B illustrate a second exemplary payload packaging arrangement.
Figure 8B:
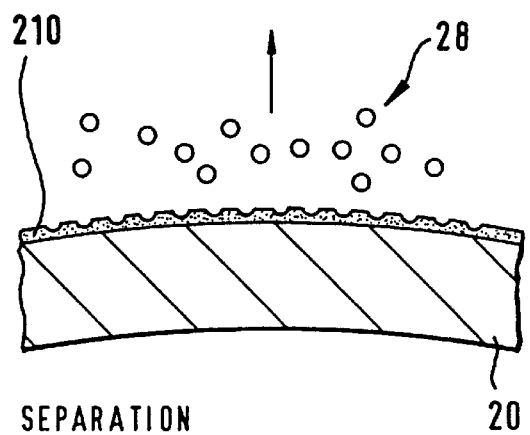

Referring now to FIGS. 8A–8B, there is shown a cross sectional view of part of an exemplary slingshot mechanism 12 to illustrate a second mechanism or technique for releasably securing a payload to the slingshot mechanism. In this technique a coating 210 of an adhesive mastic or the like is applied to the moving arm or portion of the conductive metal member 20 of the slingshot mechanism 12. The material constituting the payload 28 such as the particles or powder, is applied to the exposed surface of the coating 210, as shown in FIG. 8A, so they are retained thereon when the slingshot mechanism is in its initial, non-accelerated condition. When the metal member 20 is at or near the end of its acceleration, the payload 28 separates from the coating 210 as is shown in FIG. 8B.

Referring now to FIGS. 9A–9C, there is shown a cross sectional view of part of an exemplary slingshot mechanism 12 to illustrate a third mechanism or technique for releasably securing a payload to the slingshot mechanism. In this technique a pouch 220 is secured to the moving arm or portion of the conductive metal member 20 of the slingshot mechanism 12 using an adhesive, by heat bonding the material to the metal member or the like. The pouch 220 includes one or more rupture zones 222 or lines, which are designed to fail, when subject to certain loads and thereby rupturing or opening the pouch. As shown in FIG. 9B, when the slingshot mechanism is in its initial, non-accelerated condition, the pouch 220 is sealed and the payload 28 is retained therein.

When the pulsed current is passed through the conductive metal member 20, the pouch 220 and correspondingly the payload 28 therein is accelerated in the fashion-described hereinabove. At a point in the acceleration process the inertia of the payload 28 and/or the deformation of the metal member 20 causes each rupture zone 222 to fail thereby releasing the payload 28 for injection as shown in FIG. 9C. Once released, the payload 28 continues onto the targeted area of the body or organism.

Figure 10:
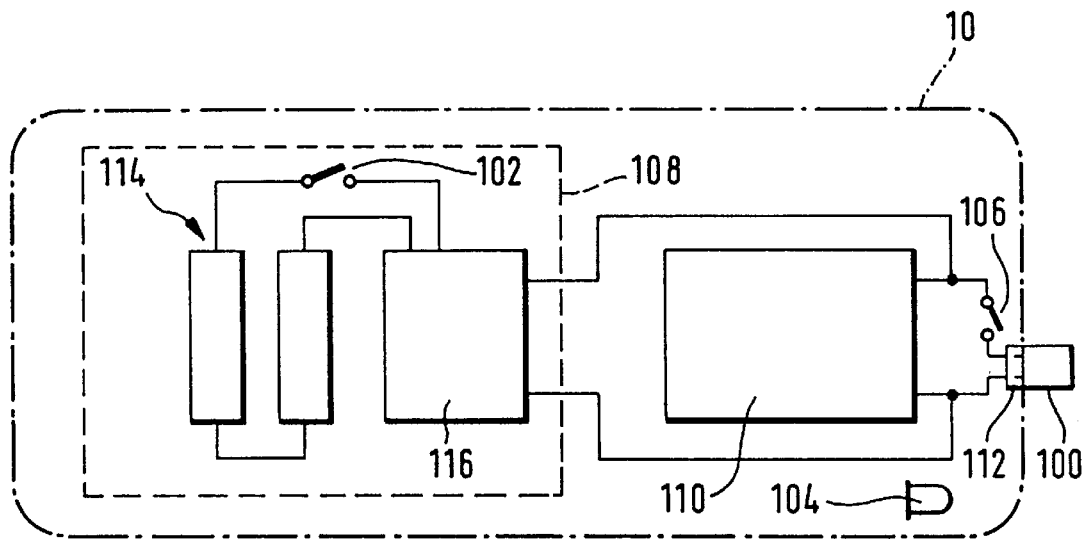
FIG. 10 is a block diagram of one embodiment of an injection device according to the instant invention.

A block diagram for one embodiment of an electromagnetic injection device 10 according to the present invention is shown in FIG. 10. The injection device 10 includes a ready light 104, an actuator switch 106, a power supply 108, a capacitor 110 and a plug connection 112 that electrically interconnects a slingshot module 100 and the electrical leads to the capacitor 110 via the actuator switch 106. In the illustrated embodiment, the injection device 10 is handheld and all the components are located in a single housing having, for example, outside dimensions on the order of about 175 millimeters long and 65 millimeters wide. As further described below, the loading, use and operation of such an injection device 10 is simple and does not require specialized training or particular knowledge of, for example, human or animal physiology.

The capacitor 110 is a high voltage, low inductance capacitor, such as that manufactured by Cornell Dubilier for exploding foil initiators, which can be charged to about 5 joules of stored energy. In particular, the capacitor has a capacitance of about 0.2–4.0 microfarads, more particularly about 1 microfarad, an inductance of about 1–10 nanohenries, more particularly about 2.5 nanohenries, and an output voltage in the range of from about 1,000 to 4,000 volts. The capacitor 110 also is capable of generating high currents on the order of 6,000 to 20,000 amperes during a discharge cycle.

The capacitor 110 is interconnected to the ready light 104 using any one of a number of techniques known in the art so the ready light is lit when the capacitor has been charged to the minimum energy level required for firing a slingshot mechanism 12. The ready light 104 is any of a number of lights known in the art for providing such visual signals including but not limited to LED's, LCD's and xenon bulbs.

Figure 14A:
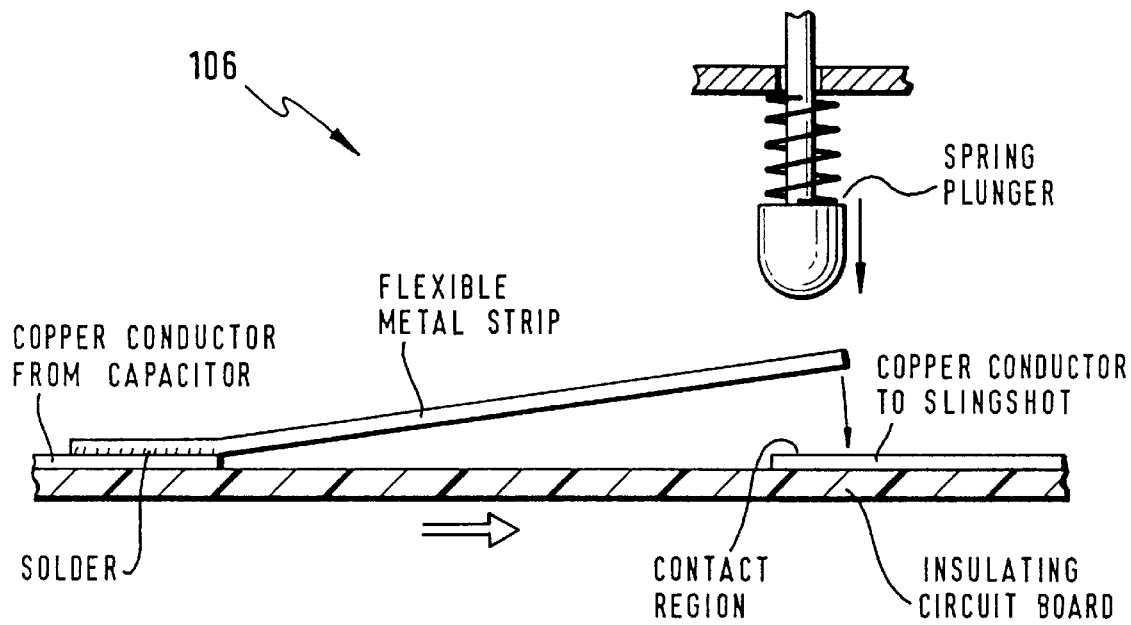
FIGS. 14A–14B are schematic views of exemplary mechanical switches.
Figure 14B:
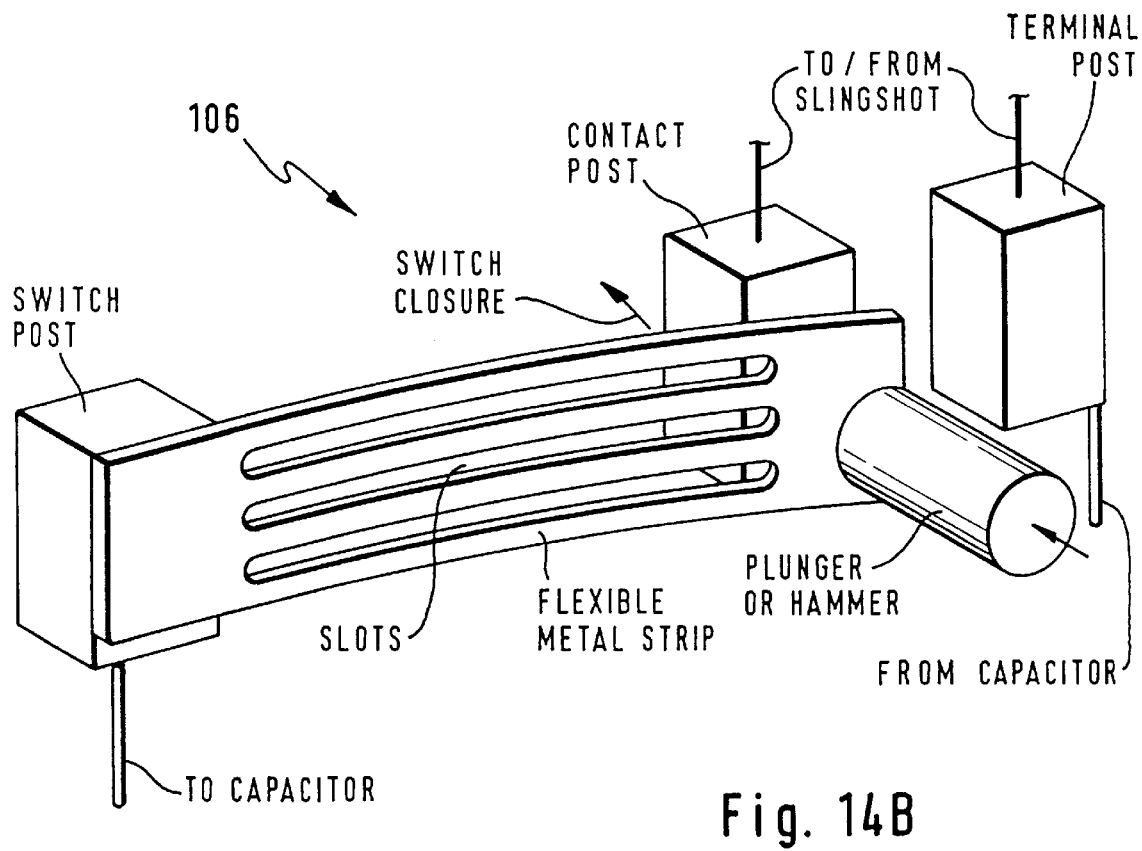

The actuator switch 106 is any one of a number of mechanical types of switches such as a common SPST toggle switch, or any other switches known in the art, including but not limited to solid state switches and triggered sparked gap switches. In particular, switches that can be repetitively opened and closed in the presence of large voltages, on the order of kilovolts, and that will pass the required currents over a discharge cycle. In a specific embodiment, the actuator switch 106 is a mechanical switch with metallic contacts having a 20 ampere rating that has been observed to generally show little damage after multiple shots in the 5,000 to 10,000 ampere pulse current range. Such switches also allow the output voltage to rise to the desired voltage on the order of tens of nanoseconds, which is adequate for a current pulse length on the order of a microsecond. Although, the actuator switch 106 preferably allows multiple shots, it is within the scope of the present invention for the injection device 10 to be configured with a single-use set of switch contacts as part of the slingshot module 100. In this way, the switch contacts would be replaced each time the slingshot module 100 is replaced. Schematic views of a some exemplary mechanical switches 106 are shown in FIGS. 14A–14B. As also indicated below, the actuator switch 106 is preferably selected so as to minimize inductive energy losses.

The plug connection 112 includes a housing and, disposed therein, any one of a number of electrical mating connections that electrically interconnect to the input leads 24 of the slingshot module 100 and which has the capability to repetitively pass the required pulse currents without failure. The housing of the plug connection 112 is configured to removably receive and support the slingshot module 100 for injection of the payload. Preferably, the plug connection housing is configured so the slingshot module is easily inserted into and removed therefrom without special tools or equipment. Also, the housing of the plug connection 112 is made from a non-conductive and non-magnetic material such as plastic to minimize inductive energy when firing the slingshot mechanism 12. Preferably, the plug connection housing is formed along with the housing of the injection device 100 so as to yield a unitary structure. Alternatively, the plug connection housing is appropriately secured to the housing of the injection device 10.

In a preferred embodiment, the electrical lines or leads between the capacitor and the slingshot module 100 are of a length and design that minimizes inductive energy losses. In addition, the capacitor 110, the actuator switch 106 and the plug connection 112 are selected so as to minimize inductive energy losses when firing the slingshot mechanism 12. Further, the electric circuit forming the current discharge path from the capacitor 110 to the slingshot mechanism 12 is designed, and the components thereof (e.g., the capacitor) are selected, so the current to the slingshot mechanism 12 peaks while the portions of the conductive metal member 20 that are to be subjected to the electromagnetic repulsive forces are close to their initial position, as shown in FIGS. 1A, 2, 3A, 4 and 5, and moving slowly. In this way, the current exerts the maximum impulse (i.e., force integrated over time) on these portions of the conductive metal member 20.

The power supply 108 can be any one of a number of sources of electrical power known to those skilled in the art which can develop the voltages and currents required to charge the capacitor 110 in a reasonable time interval, for example 10 seconds or less. For an injection device 10 that is handheld and portable, the power supply 108 preferably comprises an on/off switch 102, a DC power source 114 and a high voltage DC to DC converter 116. The DC to DC converter 116 is an electrical circuit configured using any one of a number of techniques known in the art for repetitively and reliably charging the capacitor 110 to the required capacity using a low voltage DC power source. Alternatively, the capacitor 110 can be charged from an AC power source and the converter appropriately configured electrically to convert AC voltage and current to the DC voltage and current required for charging the capacitor.

In the illustrated embodiment, the DC power source battery source 114 is a plurality of batteries, for example AA alkaline batteries, in series connection. However, the DC power source can be any of a number of systems, e.g. a system that comprises one or more batteries and be any type of battery for example a C-cell battery. Also, for multi-battery configurations the batteries can be connected in series or parallel. Further, the type of battery can be alkaline, NiCd, nickel metal hydride, or any of a number of known types of batteries. The battery selected for use preferably is conveniently available to the user and has sufficient capacity so the capacitor 110 can be charged tens of times (e.g., 50 times) before the batteries comprising the DC power source 114 would have to be replaced by the user.

The on/off switch 102 is any one of a number of switches known in the art, such as a Mini Mike Miniature Snap Action Slide switch as manufactured by ITW Switches. The on/off switch 102 preferably is disposed between the DC power source 114 and the DC to DC converter 116 so the switch interrupts low voltages and currents. However, it is within the scope of the instant invention for the on/off switch 102 to be located between the power supply 108 and the capacitor 110 so as to interrupt the voltage and currents being outputted by the power supply.

Figure 11:
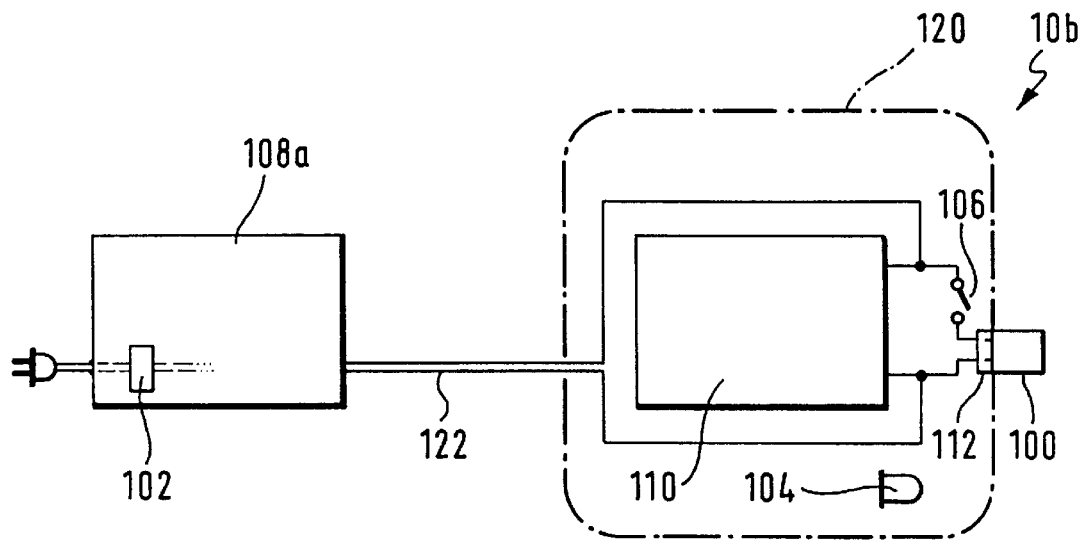
FIG. 11 is a block diagram of a second injection device embodiment.

There is shown in FIG. 11, a block diagram of a second embodiment of an injection device 10b including a handheld injection unit 120, a remotely located power supply 108a and an electrical cable 122 interconnecting the power supply 108a and the handheld injection unit 120 for charging of the capacitor 110. The handheld unit 120 includes the above described on/off switch 102, ready light 104, actuator switch 106, capacitor 110 and plug connection 112 that electrically interconnects the slingshot module 110 and the electrical leads to the capacitor 110 via the actuator switch 106.

The power supply 108a is configured to supply the voltages and currents required for charging the capacitor 110 to the required energy/capacity. In the illustrated embodiment, the power supply 108a is an AC to DC converter that is plugged into an electrical wall or floor type of socket or outlet. However, the power supply can be a variety of systems, e.g. a DC battery pack, for example a battery pack belt used in the video recording industry, with a DC to DC converter 116 as hereinabove described to supply the required voltages and currents. In an alternative embodiment, the DC to DC converter 116 is included in the handheld unit 120 so only low voltages and currents are being supplied over the cable 122. The cable 122 is any one of a number of known electrical cables that can safely and reliably handle the voltages and currents being supplied.

Figure 12:
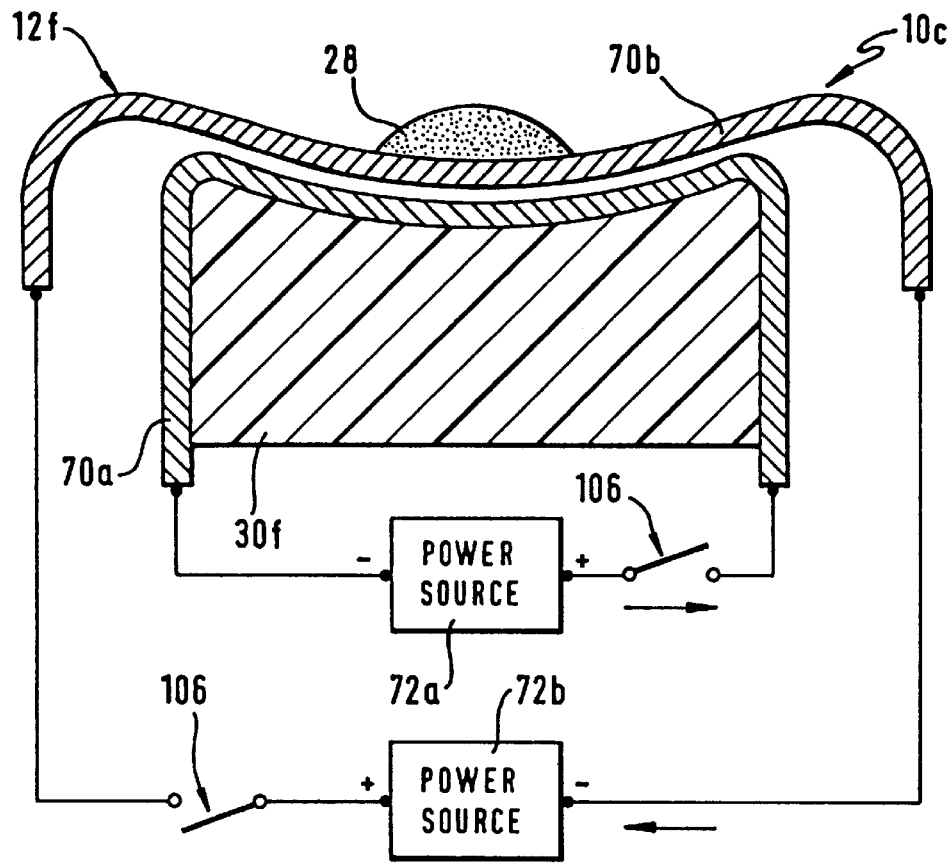
FIG. 12 is a schematic view of a third injection device embodiment.

There is shown in FIG. 12 a schematic view of a third embodiment of an electromagnetic injection device 10*c* according to the instant invention. Also illustrated is another embodiment of a slingshot mechanism 12*f*. This slingshot mechanism 12*f* includes a first conductive metal member 70*a* and a second conductive metal member 70*b* that are initially disposed parallel to each other over a pre-specified region as hereinabove described. In an exemplary embodiment, the first and second metal members 70*a,b* are arcuate and arranged so as to lie in a convex cavity in a support block 30*f*. The payload 28 is disposed at about the low point, and correspondingly at about the midpoint, of the second member 70*b*. As describe above in connection with FIGS. 3–4, the first member 70*a* is essentially stationary when a high energy current pulse is passed through it, because of the support block 30*f*, and the second member 70*b* moves repulsively away from the first member thereby accelerating the payload 28.

In this injection device embodiment, the first and second metal members 70*a,b* are each fed by a separate power source 72*a,b*. Each of these power sources 72*a,b* includes the functional components (e.g., on/off switch 102, capacitor 110) hereinabove described in connection with FIGS. 10–11 used to output a high energy current pulse. The device also is configured so as to provide synchronous current pulses to each of the first and second metal members 70*a,b* so the second member 70*b* will repulsively move away from the first member and thereby accelerate the payload releasably attached or secured to the second member. Alternatively, the first and second metal members 70*a,b* are electrically interconnected to a single power source although they are not looped together as in other described slingshot mechanism embodiments.

Although the foregoing electromagnetic injection devices 10, 10*a*, are described as having a one capacitor 110, this is not a limitation. It is within the scope of the instant invention for such an injection device to include two or more capacitors, connected electrically in series or in parallel, to develop the desired voltage and current pulses. Also, the injection device of the subject invention includes any injection device that embodies the features of the instant invention regardless of the specific arrangement of individual components. For example, a hand held injection unit can be electrically connected to an AC power source, and the hand held unit include an AC to DC converter to convert the AC voltage and currents to the voltages and currents required for charging the capacitor. Also, it is within the scope of the instant invention, for such an injection device to be configured as a one shot type of device that is disposed of after use or an injection.

A cross sectional view of an exemplary slingshot module 100 is shown in FIG. 13. The slingshot module includes a housing 150, slingshot mechanism 12, and cover member 154 that seals an aperture 152 in one end of the housing. The cover member 154 can be a foil such as polyester or Mylar that is removably secured to the housing 150. In an exemplary embodiment, the cover member 154 is a polyester film with an ethylene vinyl acetate adhesive coating, such as the Scotch Pack Heat Sealable Lid Film manufactured by 3M, that is heat sealed to the housing 150. The cover member 154 in conjunction with the housing 150 seals the aperture 152 through which the payload 28 is expelled so the payload does not become contaminated or spoiled. The housing 150 preferably is made of a material that is non-conductive and nonmagnetic including , for example, thermoplastics such as polyesters, polycarbonates and ABS, and thermosetting plastics such as phenolics and epoxies. The housing material selected also should not react with or increase the risk of contamination to the payload 28.

The slingshot mechanism 12 is disposed in the module housing 150 so the direction of acceleration for the payload 28 is essentially congruent with the axis of the housing aperture 152. Thus, when the slingshot mechanism 12 is actuated or fired by means of the pulsed current, the payload 28 is expelled through this aperture 152. To make the injection process easier, the housing preferably is designed so the distance between the initial position of the payload 28, for example, in the bent cup portion 25, and the end surface 156 of the housing, at which the cover member 154 is secured, is the desired distance between the payload and the skin of the area being targeted for injection. It should be recognized that the module 100 is not limited to the specific sling shot mechanism being illustrated and that it is within the scope of the instant invention for the slingshot module 100 to include any of the slingshot mechanisms described or referred to herein.

A recess 160 is provided in the opposite end 158 of the module housing 150, in which are exposed the input leads 24 to the slingshot mechanism 12. This end 158, the recess 160 and positioning of the input leads 24 are arranged and configured so as to mate with and be removably received by the plug connection 112 of the injection device 10,10*a*. The housing 150 also is constructed to support the slingshot mechanism 12 so it is maintained in the appropriate alignment for injection.

In the illustrated embodiment, the housing includes two interior sloping surfaces 162 that are disposed outboard of the outer arms 22. The sloping surfaces 162 are configured so as to function like a support block and restrain the motion of the outer arms 22 so they do not depart from the desired configuration during acceleration of the payload. It should be recognized that it is within the scope of the instant invention for the interior surfaces of the housing to be configured to restrain certain motion of the conductive metal member 20 as herein described or configured so as not to restrain any such motion.

The operation and use of the injection devices of the instant invention can be best understood from the following discussion and with reference to the figures hereto and the foregoing discussion. Although the injection process is described below as being in a specific sequence, it is within the scope of the invention for the described actions to be in any sequence that will result in the injection of a payload of therapeutic compounds into a body. Also, although the below-described process involves the injection of a therapeutic compound payload into a body, it is within the scope of the described method or process to inject any dry substance, as herein described, into a body or organism.

In a preferred embodiment, the manufacturer preloads, with a specified therapeutic compound or the like and at a desired dosage, in sterile packaging each slingshot module 100. However, it is within the scope of the instant invention for the slingshot mechanism 12 to be loaded in situ prior to use. The pre-loaded slingshot module 100 having the required dosage of therapeutic compound is removed from the sterile packaging and is inserted into the receptacle formed by the plug connection 112 in the device housing.

The user then closes the on/off switch 102 and the power supply 108 charges the capacitor 110. When the capacitor is charged to the required or minimum energy level required for proper actuation or firing of the slingshot mechanism 12, the ready light 104 comes on. The user removes the cover member 154 from the slingshot module 100 and locates the module aperture 152 or opening to point at the area of the body being targeted and at the appropriate distance therefrom. Preferably, as indicated above, the slingshot module 100 is designed so by pressing it to the skin, the payload 28 is located at the desired distance from the skin.

When the slingshot module 100 has been appropriately positioned, the user actuates (e.g., presses) the actuator switch 106 to electrically interconnect the capacitor 110 to the slingshot mechanism 12. The capacitor 110, when so connected, discharges a current pulse through the slingshot mechanism 12 that accelerates the payload 28 and injects it through the skin and into the subcutaneous tissues as hereinabove described.

After injecting the payload 28, the spent slingshot module 100 is removed from the injection device 10 and discarded by the user. The spent slingshot module 100 can be disposed off in the same way as any article coming in contact with the skin can be disposed off. However, and in contrast to hypodermic syringes and the needles there for, the spent slingshot module 100 is not automatically treated and handled as bio-hazardous material. Additionally, special disposal precautions need not be taken, as is done with hypodermic syringes and/or the needles there for, because the slingshot module 100 does not use sharp or pointed surfaces to penetrate the skin to inject the payload.

If required, the user then obtains a fresh, charged slingshot module 100 for the next injection and this replacement slingshot module 100 is inserted into the plug connection 112 as described above. Thereafter the above-described process of locating, firing, and discarding is repeated. It is within the scope of the instant invention for the capacitor 110 to begin re-charging the capacitor 110 automatically following a discharge or to manually control the re-charging of the capacitor 110 following each injection.

Although a preferred embodiment of the invention has been described using specific terms, such description is for illustrative purposes only, and it is to be understood that changes and variations may be made without departing from the spirit or scope of the following claims.

What is claimed is:

1. A method for accelerating an object, comprising the steps of:
   providing a force generating device that generates an external force by means of electromagnetic repulsion, where the force generating device generates the external force by means of electromagnetic repulsion of at least one conductive member;
   generating the external force using the force generating device; and
   accelerating the object by means of the generated external force.

2. A method for injection of a payload into tissues of an organism, comprising the steps of:
   generating a force by means of electromagnetic repulsion of at least one conductive member;
   wherein said step of generating includes passing anti-parallel currents through the at least one conductive member; and
   accelerating the payload to be injected, by means of the generated force to a velocity sufficient for the payload to pass through the skin of the organism.

3. A method for injection of a payload into tissues of an organism, comprising the steps of:
   generating a force by means of electromagnetic repulsion of at least one conductive member;
   wherein said step of generating includes passing anti-parallel currents through the at least one conductive member;
   accelerating the payload to be injected, by means of the generated force, to a velocity sufficient for the payload to pass through the skin of the organism; and
   wherein the payload to be injected is external to the electromagnetic repulsion that generates the force.

4. A method for accelerating an object, comprising the steps of:
   providing a force generating device that generates an external force by means of electromagnetic repulsion;
   generating the external force using the force generating device;
   accelerating the object by means of the generated external force; and
   wherein the force generating device generates the external force in a predetermined direction electromagnetically and repulsively responsive to anti-parallel electric currents flowing through the device and said step of generating includes passing the anti-parallel electric currents through the electromagnetic force-generating device thereby generating the external force used for accelerating the object.

5. The method of claim 4, wherein the force generating device being provided includes a conductive member that is configured to have at least one pair of adjacent arms interconnected to each other, wherein the passing of the anti-parallel electric currents includes passing an electric current through the at least one pair of adjacent arms so the current in one adjacent arm is anti-parallel to the current flowing through the other adjacent arm, whereby the at least one pair of adjacent arms are electromagnetically, repulsively moved apart from each other.

6. The method of claim 4, further comprising releasably attaching the object to a portion of the force generating device so the object is accelerated by the external force being generated to a desired velocity and then released therefrom.

7. A method for injection of a payload into tissues of an organism, comprising the steps of:
   generating a force by means of electromagnetic repulsion of at least one conductive member;
   wherein said step of generating including passing an electric current through the at least one conductive member so as to cause the electromagnetic repulsion thereof that generates the force;
   wherein said conductive member being configured so as to have at least one pair of adjacent arms interconnected to each other;
   wherein said step of passing includes passing the electric current through the at least one pair of adjacent arms so the current in one adjacent arm is anti-parallel to the current flowing through the other adjacent arm, whereby the at least one pair of adjacent arms are electromagnetically, repulsively moved apart from each other so as to generate the force; and
   accelerating the payload to be injected, by means of the generated force to a velocity sufficient for the payload to pass through the skin of the organism.

8. The injection method of claim 7, wherein the at least one conductive member is configured so as to have two pairs of adjacent arms each pair being interconnected by a curved portion so as to form a M shape, and wherein said method further includes the steps of:

disposing the payload in the curved portion; and electromagnetically repulsively moving each pair of adjacent arms apart from each other so as to cause the curved portion therebetween to accelerate in a given direction and thereby accelerate the payload.

9. The injection method of claim 7, wherein the at least one conductive member is configured so as to have a pair of adjacent arms, first and second arms, and wherein said method further includes the steps of:

disposing the payload at about the midpoint of a long side of the first arm, restraining the second arm from moving in a direction away from the first arm, and electromagnetically repulsively moving the first arm away from the second arm to accelerate the payload in a given direction.

10. The injection method of claim 7, wherein the at least one conductive member is configured so as to have first, second and third arms, each having two ends, wherein the first end of the first arm is interconnected to the first end of the second arm so the first and second arms are in opposed relationship, wherein the second end of the first arm is interconnected to the first end of the third arm so the first and third arms also are in opposed relationship, and wherein said step of passing includes passing the electric current through the first, second and third arms so the current flowing in the first arm is anti-parallel to the current flowing through both the second and third arms, whereby the first arm is electromagnetically, repulsively moved with respect to the second and third arms.

11. The injection method of claim 10, wherein said method further includes the steps of:

disposing the payload at about the midpoint of a side of the first arm, restraining the second and third arms from moving in a direction away from the first arm, and electromagnetically repulsively moving the first arm away from the second arm and third arms to accelerate the payload in a given direction.

12. An electromagnetic transdermal injection device that injects a payload into tissues of an organism, comprising:

a force generating mechanism that generates at least a predetermined force in a predetermined direction by means of electromagnetic repulsion responsive to anti-parallel electric currents flowing in the force generating mechanism; and wherein the payload is releasably attached to a portion of the force generating mechanism so the payload is accelerated to a velocity, the velocity required for injection of the payload into the tissues, by the predetermined force and then released therefrom.

13. The electromagnetic transdermal injection device of claim 12, wherein the force generating mechanism includes a conductive member that is configured geometrically so the conductive member generates a force in a predetermined direction electromagnetically and repulsively responsive to a short duration high voltage high current pulse and wherein the payload is releasably attached to a portion of the conductive member so the payload is accelerated to the velocity required for injection.

14. The electromagnetic transdermal injection device of claim 12, further comprising an electrical power supply configured to provide one or more short duration high voltage and high current pulses; and a switch that selectively, electrically interconnects the power supply and the force generating mechanism.

15. The electromagnetic transdermal injection device of claim 14, wherein the electrical power supply includes a high voltage, low inductance capacitor.

16. The electromagnetic transdermal injection device of claim 14, wherein the switch is a SPST type of mechanical switch with metal contacts.

17. The device of claim 12, wherein the force generating mechanism comprises a conductive member with a first and a second portion which are geometrically arranged to each other such that a current through the conductive member runs essentially anti-parallel in said first and said second portions thereby generating an electromagnetic, repulsive force between said portions.

18. The device of claim 12, wherein the force generating mechanism comprises at least two opposing conductive members and means for applying current to each of said at least two opposing conductive members so as to generate the predetermined force.

19. The electromagnetic transdermal injection device of claim 12, wherein the payload to be injected is at least one of solids, gels, liquids absorbed into porous solids, encapsulated liquids, dry powder or particles.

20. The electromagnetic transdermal injection device of claim 19, wherein the payload to be injected includes at least one of an active material selected from the group consisting of therapeutic agents, including antibiotics, insulin, proteins an analgesics, and DNA.

* * * * *